United States Patent [19]
Shibatani et al.

[11] Patent Number: 5,922,568
[45] Date of Patent: *Jul. 13, 1999

[54] GENE PARTICIPATING IN THE MECHANISM OF SECRETION OF ESTERASE

[76] Inventors: Takeji Shibatani, No. 3-8-15, Uzumoridai, Higashinada-ku, Kobe-shi, Hyogo-ken; Hiroyuki Akatsuka, No. 4-19-13-1301, Satanakamachi, Moriguchi-shi, Osaka-fu; Eri Kawai, No. 3-39-151, Higashiyagura, Kusatsu-shi, Shiga-ken, all of Japan

[ * ] Notice: This patent is subject to a terminal disclaimer.

[21] Appl. No.: 09/005,232

[22] Filed: Jan. 9, 1998

Related U.S. Application Data

[63] Continuation-in-part of application No. 08/620,605, Mar. 22, 1996.

[51] Int. Cl.⁶ .............................. C12P 21/06; C12N 1/20; C12N 9/16; C07H 21/04
[52] U.S. Cl. ........................ 435/69.1; 536/23.1; 536/23.7; 435/252.3; 435/320.1; 435/196; 435/880; 530/350
[58] Field of Search ..................... 435/69.1, 196, 435/252.33, 320.1, 880; 536/23.1, 23.7; 530/350

[56] References Cited

U.S. PATENT DOCUMENTS 5,846,811 12/1998 Shibatani et al. ................ 435/252.33

FOREIGN PATENT DOCUMENTS

0446771A2 9/1991 European Pat. Off. .
0544250A2 6/1993 European Pat. Off. .

OTHER PUBLICATIONS

Akatsuka, et al., "The Three Genes lipB, lipC, and lipD Involved in the Extracellular Secretion of *Serratia marcescens* Lipase Which Lacks an N–Terminal Signal Peptide," Journal of Bacteriology, vol. 177, No. 22 (Nov. 1995) pp. 6381–6389.

*Primary Examiner*—Robert A. Wax
*Assistant Examiner*—Tekchand Saidha

[57] ABSTRACT

An isolated gene encoding a polypeptide which is required for secretion of esterase originated from a microorganism of the genus Serratia, a recombinant plasmid comprising a plasmid prepared by inserting the isolated gene into a vector plasmid, a microorganism transformed with the recombinant plasmid, and a method for the production of an esterase which comprises cultivating the transformant microorganism as set forth above in a medium and collecting the produced esterase outside and inside the cells. The transformed microorganism have remarkably excellent capability of extracellular secretion of esterase.

12 Claims, 1 Drawing Sheet

```
                            SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 4547 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
         (B) STRAIN: Serratia marcescens Sr41

(xi) SEQUENCE DESCRIPTION: SEQ ID NO:1:

GTGAATCAAT TTATCCCGCG CAACGAAATT GCGGATGTTA TACGTACACG CAGCAAAGTC      60

TTCTGGACCG TTGGTATATT TACTGCGTTT ATTAACCTGT TAATGCTGGT TCCTTCCATT     120

TATATGCTCC AGGTTTACGA CCGGGTGCTG CCTTCGCGCA ATGAAATCAC GCTGTTAATG     180

CTGACGCTGA TCATGCTGGG CATGTTCGGC ATGATGTCGC TGTTGGAATA CGTGCGCAGC     240

ATGGTGGTGA TCCGCATCGG CAGCCAGCTG GATATGCGTC TCAACACGCG AGTCTATACC     300

GCGGCCTACG AAGCGAATCT GAAAAACGGT TCGTCTGACG CCGGTCAGAT GCTGAGCGAT     360

TTGACCAATC TGCGCCAATT CCTCACCGGT AGCGCGCTGT TCGCCTTCTT TGATGCGCCG     420

TGGTTTCCGA TCTATCTGTT GGTGATATTC CTCTTTAACC CTTGGTTGGG CCTTTTCGCC     480

CTGGTCGGTG CGCTGTTGCT GATCGCATTG GCGGTAATCA ATGAAGTGGT TTCGAAAAAG     540

CCGCTGGGAG AAGCCAGCAA GCTGTCGATC ATGTCAGGTA ATTTGGCCAG CACCAATCTG     600

CGAAATGCCG AAGTGATCGA GGCTTTGGGG ATGTTGCCTA ACCTGAAACG CCGGTGGTTC     660

GGTCTGCACC AGCGGTTCTT GAACAGCCAA CGCATCGCCA GCGAACGCGC ATCGCGGGTC     720

ACGTCAATCA CCAAGTTCGT GCGTATGTCG CTGCAGTCCT TAGTGTTGGG CCTGGGGGGA     780

TGGTTGGCGA TTGATGGGCA CATCACGCCC GGCATGATGA TCGCCGGTTC TATATTGATG     840

GGGCGAACGT TGGCGCCGAT CGAGCAGGTC ATTAACGTTT GGAAAAGCTA TAGCGCGGCC     900

AAACTTTCTT ATGGCCGCTT GGTCAAGCTG CTGGAAACGC ATCCGCAGCG TGGTACCGGC     960

ATGTCGCTGC CGCGTCCGGA AGGTGTGCTC TCCGTAGAAG GCGTGACCGC CACGCCTCCG    1020

GGATCGAAAG GGGATGCGGT GCTGCATAAC GTAAGTTTTG CCATTCAACC CGGCGATGTG    1080

CTGGGGATTA TCGGTCCGAG TGCGTCGGGC AAATCAACAT TGGCGCGCTT ACTGGTCGGT    1140

ATTTGGCCTG TGAGCGAAGG GATAGTGCGG TTGGATAATG CCGACATCTA CCAGTGGAAC    1200

AAAGACGAAC TGGGGCCCTA TATCGGCTAT CTGCCGCAGG ACATCGAGTT GTTCGCCGGC    1260

ACTATCGCCG AGAACATCGC TCGCTTTAAC GACATCGATT CAGAGAAAGT GATTGAGGCT    1320

GCCAAGCTGG CTGGTGTGCA TGAACTGATC CTGCGTTTCC CTAACGGTTA CGATTCGGTG    1380

ATCGGCAACG GTGGTGCAGG GTTGTCCGGC GGGCAGAAGC AACGTATCGG CCTGGCGCGG    1440

GCATTGTATG GCGATCCCGC GTTGGTGGTG TTGGATGAGC CTAACTCCAA CCTGGATGAT    1500
```

```
GCCGGCGAGA AAGCGTTGAA CCAGGCCATC ATGTTCCTTA AACAGCGTAA TAAGACGGTG    1560

GTCCTGATCA CTCACCGCAC CAATCTGCTG TCGATGACCA GCAAGCTGTT GCTGTTGGTT    1620

AACGGGAACG TCAATGCATT CGGCCCAACG CAGCAGGTGC TGCAGGCGTT GGCGAATGCG    1680

CAAAAAGCGC AGGTGCCTCC GCAGGCGGTG CGTGCGGTGA ACTCCGAGCC GGATGAAGGC    1740

GAAATCCCTA AAACTCAAAT TAATTAAGCC GTGAACTTGC CCGGCGGCGC TTTTGCGTCG    1800

CCGACAGTCA AAGGAGTTGG TATGTCTACG CATATTGGCG AGCCGCAAGA CTCGTATACT    1860

GAAGAGATCC CACAAGATGA ACGGCGGTTT ACCCGTATGG GGTGGCTGGT GGTCGGGATC    1920

GGTCTGTTCG GGTTTTTAGC CTGGGCGGCC TTTGCGCCGT TGGATAAAGG GGTGGCGTCG    1980

CCGGGATCGG TAACCGTTTC CGGCAACCGC AAAACGGTGC AGGCCCCGGC CAGCGGCATC    2040

ATTAAGAATA TTGCGGTCAG AGATGGCGAC AAAGTGAAAG CCGGTGAGGT GCTGGTGCAG    2100

CTCAGCCAGG TGCAGGCTCA AGCTCAGGTT GATTCGCTGC GGGATCAGTA CTACACCACG    2160

CTGGCGACAG AAGGGCGCTT GCTGGCAGAA CGCGATGGGT TGAGCATAGT GACTTTCTCA    2220

CCCATTTTGG ACGCGGTGAA AGATAAACCT CGCGTGGCAG AAATCATTGC ATTGCAAACG    2280

CAGCTGTTCG CCTCCCGCCG CCAAGCGCTG CAAAGTGAAA TCGACGGCTA TAAGCAGTCA    2340

ATGGACGGAA TCCGTTTCCA ATTAAAAGGA CTGCAGGATT CGCGCGGTAA CAAACAGATC    2400

CAGCTTTCCA GCCTGCGTGA GCAGATGAAC AGCATGAAGC AGTTGGCGGC GGACGGTTAC    2460

CTACCGCGTA ACCGTTACCT GGAAGTGCAG CGCCAGTTTG CCGAGGTAAA TAGCAGCATT    2520

GATGAAACGG TGGGCGGAT TGGCCAATTG CAAAAGCAGT TGCTGGAATC ACAGCAACGC    2580

ATCGATCAGC GTTTCGCCGA CTACCAGCGC GAAGTCAGAA CGCAGCTGGC GCAAACTCAA    2640

ATGGACGCCA GCGAATTCCG CAACAAGCTG CAAATGGCCG ATTTCGATCT GGGCAACACC    2700

GCCATCACCT CACCGGTGGA CGGCACCGTG GTTGGATTGA ATATCTTCAC TCAGGGGGC    2760

GTCGTGGGAG CGGGTGACCA CCTGATGGAC GTTGTGCCCA GCCAGGCGAC TTTGGTGGTG    2820

GATTCTCGCC TCAAAGTCGA CCTGTTCGAT AAGGTGTACA ACGGGTTGCC GGTGGATCTG    2880

ATGTTTACCG CCTTCAACCA AAACAAAACC CCGAAAATTC CGGGAACCGT CACCTTGGTT    2940

TCCGCCGACC GCCTGGTCGA CAAAGCCAAT GGCGAACCTT ACTACCAGAT GCAGGTCACG    3000

GTCTCGCCGG AGGGCATGAA AATGCTCAGT GGCGAGGACA TCAAGCCGGG GATGCCGGTG    3060

GAGGTGTTCG TGAAAACGGG GTCGCGCTCG CTGTTGAGCT ATCTGTTTAA ACCTATTTTG    3120

GATCGCGCTC ATACTTCATT AACCGAGGAA TAATTTTGAT TCATTCAAAA CGACAGGCTG    3180

CCGGTCTGGT TATCGGCACC CTTTTGTTTG CGATGTCTGC GCCGGTTTAT TCGATAGGGA    3240

TTTTAGACGC ATATTCGCTG GCATTAGAAA AGGACCCGAC CTTTCGGGCG CTATAAAAG    3300

AGAAAGAAGC GGGAGATGAA AACGAAAATA TCGGCAGGGC AGGGCTGCTG CCGAAGGTAT    3360

CGCTGAACTA CCAGAATTCG CCGCGCAACT GGCAAACTCA GAAGTACCCG CAAAGCGACT    3420

TTTTCGGCAA TGTTTCGGAG GTTACCCGGC GGCAGCAATA TCGCAGCTAT TCCAGTTCGA    3480

TCACCTTGAC GCAGCCGCTG TTCGATTATG AAGCTTACGC CAGGTACAAA GCCGGCGTGG    3540

CGCAGACCAT GATGTCGGAC GAGACGTATC GCGGTAAGTT GCTGGATTTG GCGGTGAGGG    3600

TGATTAACGC CTATGTCGAA GTGGCTTATT CCAAGGATCA AATCGCGTTG GCCGAAGCTC    3660

AAAAGGCGGC TTACAAGGAA CAGCTGACTT TGAACGATCG CCTGATGAGC GCCGGTGAAG    3720

GTACCATTAC CGACGTATCC GAAACTCAGG CGCGCTATAG CCTGGCTGAA GCACAGGTGA    3780

TAGAAGCGCG CGATGCACTG GATGCCGCAC AGCGTGAATT GGAAGTAATT ATCGGCATGC    3840

CGCTGAACCA ACTGGATGAA TTGCAGGTCT TGCGGCCGGG TAAATTCAAA GTGGCGCCGT    3900
```

-continued

```
TAATCCCGTC CAAGTTCGAA GAGTGGCAAA AGATCGCGTT GGAGAACAAC CCTGTATTGG    3960

CCGCCTCGCG TCATGGCGTG GATGCTGCTA AGTATGATGT CGAAAGGAAA CGGGCTGGCT    4020

TTATGCCACA GGTTCAGCTG TATGCTTCGC ATTCGGAAAA CGACGCCAGC AGCGACAACA    4080

CGGTTAACCA GAAATACCGT ACTGACAGCA TTGGCGTGCA GGTCAGCATG CCTATTTATT    4140

CCGGTGGCGG TGTTTCGGCA TCGACCCGCC AGGCAGCGGC GCGTTACGGG CAAGCGATGT    4200

ATGAAATGGA TGCGCAAACG GGCACCACGC TCAACGATCT GCGCAAACAG TACAATTTGT    4260

GTATTAGCAG CAGCGCTAAA GTGGCGGCCT ATGAACTGGC GGTTCAATCG GCGACGACCC    4320

AGGTGACGGC GACCCGGCAA AGCGTGCTGG CTGGGCAACG TGTCAACGTC GATGTGCTCA    4380

ATGCCGAACA GCAGCTCTAT AGCGCACAGG CGATTTTGGC CTCTGCTAAA TACACTTATA    4440

TCAAATCCTG GATCACCCTA TTGAGTGACT CCGGCACGTT AGACGAGAAA GATGTACTGC    4500

GCGTGGCGCA GTATTTTTAC CCGCAATCGA TAACAACATA TTCACTA                 4547
```

(2) INFORMATION FOR SEQ ID NO:2:

(i) SEQUENCE CHARACTERISTICS:
        (A) LENGTH: 588 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Val Asn Gln Phe Ile Pro Arg Asn Glu Ile Ala Asp Val Ile Arg Thr
  1               5                  10                  15

Arg Ser Lys Val Phe Trp Thr Val Gly Ile Phe Thr Ala Phe Ile Asn
             20                  25                  30

Leu Leu Met Leu Val Pro Ser Ile Tyr Met Leu Gln Val Tyr Asp Arg
         35                  40                  45

Val Leu Pro Ser Arg Asn Glu Ile Thr Leu Leu Met Leu Thr Leu Ile
     50                  55                  60

Met Leu Gly Met Phe Gly Met Met Ser Leu Leu Glu Tyr Val Arg Ser
 65                  70                  75                  80

Met Val Val Ile Arg Ile Gly Ser Gln Leu Asp Met Arg Leu Asn Thr
                 85                  90                  95

Arg Val Tyr Thr Ala Ala Tyr Glu Ala Asn Leu Lys Asn Gly Ser Ser
            100                 105                 110

Asp Ala Gly Gln Met Leu Ser Asp Leu Thr Asn Leu Arg Gln Phe Leu
        115                 120                 125

Thr Gly Ser Ala Leu Phe Ala Phe Phe Asp Ala Pro Trp Phe Pro Ile
    130                 135                 140

Tyr Leu Leu Val Ile Phe Leu Phe Asn Pro Trp Leu Gly Leu Phe Ala
145                 150                 155                 160

Leu Val Gly Ala Leu Leu Leu Ile Ala Leu Ala Val Ile Asn Glu Val
                165                 170                 175

Val Ser Lys Lys Pro Leu Gly Glu Ala Ser Lys Leu Ser Ile Met Ser
            180                 185                 190

Gly Asn Leu Ala Ser Thr Asn Leu Arg Asn Ala Glu Val Ile Glu Ala
        195                 200                 205

Leu Gly Met Leu Pro Asn Leu Lys Arg Arg Trp Phe Gly Leu His Gln
    210                 215                 220

Arg Phe Leu Asn Ser Gln Arg Ile Ala Ser Glu Arg Ala Ser Arg Val
225                 230                 235                 240
```

-continued

```
Thr Ser Ile Thr Lys Phe Val Arg Met Ser Leu Gln Ser Leu Val Leu
            245                 250                 255
Gly Leu Gly Gly Trp Leu Ala Ile Asp Gly His Ile Thr Pro Gly Met
        260                 265                 270
Met Ile Ala Gly Ser Ile Leu Met Gly Arg Thr Leu Ala Pro Ile Glu
        275                 280                 285
Gln Val Ile Asn Val Trp Lys Ser Tyr Ser Ala Ala Lys Leu Ser Tyr
290                 295                 300
Gly Arg Leu Val Lys Leu Leu Glu Thr His Pro Gln Arg Gly Thr Gly
305                 310                 315                 320
Met Ser Leu Pro Arg Pro Glu Gly Val Leu Ser Val Glu Gly Val Thr
                325                 330                 335
Ala Thr Pro Pro Gly Ser Lys Gly Asp Ala Val Leu His Asn Val Ser
                340                 345                 350
Phe Ala Ile Gln Pro Gly Asp Val Leu Gly Ile Ile Gly Pro Ser Ala
            355                 360                 365
Ser Gly Lys Ser Thr Leu Ala Arg Leu Leu Val Gly Ile Trp Pro Val
370                 375                 380
Ser Glu Gly Ile Val Arg Leu Asp Asn Ala Asp Ile Tyr Gln Trp Asn
385                 390                 395                 400
Lys Asp Glu Leu Gly Pro Tyr Ile Gly Tyr Leu Pro Gln Asp Ile Glu
                405                 410                 415
Leu Phe Ala Gly Thr Ile Ala Glu Asn Ile Ala Arg Phe Asn Asp Ile
                420                 425                 430
Asp Ser Glu Lys Val Ile Glu Ala Lys Leu Ala Gly Val His Glu
            435                 440                 445
Leu Ile Leu Arg Phe Pro Asn Gly Tyr Asp Ser Val Ile Gly Asn Gly
        450                 455                 460
Gly Ala Gly Leu Ser Gly Gln Lys Gln Arg Ile Gly Leu Ala Arg
465                 470                 475                 480
Ala Leu Tyr Gly Asp Pro Ala Leu Val Val Leu Asp Glu Pro Asn Ser
                485                 490                 495
Asn Leu Asp Asp Ala Gly Glu Lys Ala Leu Asn Gln Ala Ile Met Phe
                500                 505                 510
Leu Lys Gln Arg Asn Lys Thr Val Val Leu Ile Thr His Arg Thr Asn
            515                 520                 525
Leu Leu Ser Met Thr Ser Lys Leu Leu Leu Val Asn Gly Asn Val
        530                 535                 540
Asn Ala Phe Gly Pro Thr Gln Gln Val Leu Gln Ala Leu Ala Asn Ala
545                 550                 555                 560
Gln Lys Ala Gln Val Pro Pro Gln Ala Val Arg Ala Val Asn Ser Glu
                565                 570                 575
Pro Asp Glu Gly Glu Ile Pro Lys Thr Gln Ile Asn
            580                 585
```

(2) INFORMATION FOR SEQ ID NO:3:

(i) SEQUENCE CHARACTERISTICS:
  (A) LENGTH: 443 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:3:

Met Ser Thr His Ile Gly Glu Pro Gln Asp Ser Tyr Thr Glu Glu Ile

```
              1               5                    10                        15
        Pro Gln Asp Glu Arg Arg Phe Thr Arg Met Gly Trp Leu Val Val Gly
                        20                  25                  30

Ile Gly Leu Phe Gly Phe Leu Ala Trp Ala Ala Phe Ala Pro Leu Asp
                    35                  40                  45

Lys Gly Val Ala Ser Pro Gly Ser Val Thr Val Ser Gly Asn Arg Lys
                50                  55                  60

Thr Val Gln Ala Pro Ala Ser Gly Ile Ile Lys Asn Ile Ala Val Arg
        65                  70                  75                  80

Asp Gly Asp Lys Val Lys Ala Gly Glu Val Leu Val Gln Leu Ser Gln
                        85                  90                  95

Val Gln Ala Gln Ala Gln Val Asp Ser Leu Arg Asp Gln Tyr Tyr Thr
                        100                 105                 110

Thr Leu Ala Thr Glu Gly Arg Leu Leu Ala Glu Arg Asp Gly Leu Ser
                    115                 120                 125

Ile Val Thr Phe Ser Pro Ile Leu Asp Ala Val Lys Asp Lys Pro Arg
                    130                 135                 140

Val Ala Glu Ile Ile Ala Leu Gln Thr Gln Leu Phe Ala Ser Arg Arg
        145                 150                 155                 160

Gln Ala Leu Gln Ser Glu Ile Asp Gly Tyr Lys Gln Ser Met Asp Gly
                        165                 170                 175

Ile Arg Phe Gln Leu Lys Gly Leu Gln Asp Ser Arg Gly Asn Lys Gln
                        180                 185                 190

Ile Gln Leu Ser Ser Leu Arg Glu Gln Met Asn Ser Met Lys Gln Leu
                        195                 200                 205

Ala Ala Asp Gly Tyr Leu Pro Arg Asn Arg Tyr Leu Glu Val Gln Arg
                        210                 215                 220

Gln Phe Ala Glu Val Asn Ser Ser Ile Asp Glu Thr Val Gly Arg Ile
        225                 230                 235                 240

Gly Gln Leu Gln Lys Gln Leu Leu Glu Ser Gln Gln Arg Ile Asp Gln
                        245                 250                 255

Arg Phe Ala Asp Tyr Gln Arg Glu Val Arg Thr Gln Leu Ala Gln Thr
                        260                 265                 270

Gln Met Asp Ala Ser Glu Phe Arg Asn Lys Leu Gln Met Ala Asp Phe
                        275                 280                 285

Asp Leu Gly Asn Thr Ala Ile Thr Ser Pro Val Asp Gly Thr Val Val
                    290                 295                 300

Gly Leu Asn Ile Phe Thr Gln Gly Gly Val Val Gly Ala Gly Asp His
        305                 310                 315                 320

Leu Met Asp Val Val Pro Ser Gln Ala Thr Leu Val Val Asp Ser Arg
                        325                 330                 335

Leu Lys Val Asp Leu Phe Asp Lys Val Tyr Asn Gly Leu Pro Val Asp
                        340                 345                 350

Leu Met Phe Thr Ala Phe Asn Gln Asn Lys Thr Pro Lys Ile Pro Gly
                    355                 360                 365

Thr Val Thr Leu Val Ser Ala Asp Arg Leu Val Asp Lys Ala Asn Gly
                    370                 375                 380

Glu Pro Tyr Tyr Gln Met Gln Val Thr Val Ser Pro Glu Gly Met Lys
        385                 390                 395                 400

Met Leu Ser Gly Glu Asp Ile Lys Pro Gly Met Pro Val Glu Val Phe
                        405                 410                 415

Val Lys Thr Gly Ser Arg Ser Leu Leu Ser Tyr Leu Phe Lys Pro Ile
                    420                 425                 430
```

Leu Asp Arg Ala His Thr Ser Leu Thr Glu Glu
        435                 440

(2) INFORMATION FOR SEQ ID NO:4:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Leu Ile His Ser Lys Arg Gln Ala Ala Gly Leu Val Ile Gly Thr Leu
1               5                   10                  15

Leu Phe Ala Met Ser Ala Pro Val Tyr Ser Ile Gly Ile Leu Asp Ala
                20                  25                  30

Tyr Ser Leu Ala Leu Glu Lys Asp Pro Thr Phe Arg Ala Ala Ile Lys
            35                  40                  45

Glu Lys Glu Ala Gly Asp Glu Asn Glu Asn Ile Gly Arg Ala Gly Leu
    50                  55                  60

Leu Pro Lys Val Ser Leu Asn Tyr Gln Asn Ser Pro Arg Asn Trp Gln
65                  70                  75                  80

Thr Gln Lys Tyr Pro Gln Ser Asp Phe Phe Gly Asn Val Ser Glu Val
                85                  90                  95

Thr Arg Arg Gln Gln Tyr Arg Ser Tyr Ser Ser Ile Thr Leu Thr
                100                 105                 110

Gln Pro Leu Phe Asp Tyr Glu Ala Tyr Ala Arg Tyr Lys Ala Gly Val
                115                 120                 125

Ala Gln Thr Met Met Ser Asp Glu Thr Tyr Arg Gly Lys Leu Leu Asp
    130                 135                 140

Leu Ala Val Arg Val Ile Asn Ala Tyr Val Glu Val Ala Tyr Ser Lys
145                 150                 155                 160

Asp Gln Ile Ala Leu Ala Glu Ala Gln Lys Ala Ala Tyr Lys Glu Gln
                165                 170                 175

Leu Thr Leu Asn Asp Arg Leu Met Ser Ala Gly Glu Gly Thr Ile Thr
                180                 185                 190

Asp Val Ser Glu Thr Gln Ala Arg Tyr Ser Leu Ala Glu Ala Gln Val
                195                 200                 205

Ile Glu Ala Arg Asp Ala Leu Asp Ala Ala Gln Arg Glu Leu Glu Val
    210                 215                 220

Ile Ile Gly Met Pro Leu Asn Gln Leu Asp Glu Leu Gln Val Leu Arg
225                 230                 235                 240

Pro Gly Lys Phe Lys Val Ala Pro Leu Ile Pro Ser Lys Phe Glu Glu
                245                 250                 255

Trp Gln Lys Ile Ala Leu Glu Asn Asn Pro Val Leu Ala Ala Ser Arg
                260                 265                 270

His Gly Val Asp Ala Ala Lys Tyr Asp Val Glu Arg Lys Arg Ala Gly
            275                 280                 285

Phe Met Pro Gln Val Gln Leu Tyr Ala Ser His Ser Glu Asn Asp Ala
    290                 295                 300

Ser Ser Asp Asn Thr Val Asn Gln Lys Tyr Arg Thr Asp Ser Ile Gly
305                 310                 315                 320

Val Gln Val Ser Met Pro Ile Tyr Ser Gly Gly Val Ser Ala Ser
                325                 330                 335

Thr Arg Gln Ala Ala Ala Arg Tyr Gly Gln Ala Met Tyr Glu Met Asp

-continued

|  | | | 340 | | | | 345 | | | | 350 | | |
|---|---|---|---|---|---|---|---|---|---|---|---|---|---|
| Ala | Gln | Thr | Gly | Thr | Thr | Leu | Asn | Asp | Leu | Arg | Lys | Gln | Tyr | Asn | Leu |
| | | 355 | | | | | 360 | | | | 365 | | | | |
| Cys | Ile | Ser | Ser | Ser | Ala | Lys | Val | Ala | Ala | Tyr | Glu | Leu | Ala | Val | Gln |
| | 370 | | | | | 375 | | | | | 380 | | | | |
| Ser | Ala | Thr | Thr | Gln | Val | Thr | Ala | Thr | Arg | Gln | Ser | Val | leu | Ala | Gly |
| 385 | | | | | 390 | | | | | 395 | | | | | 400 |
| Gln | Arg | Val | Asn | Val | Asp | Val | Leu | Asn | Ala | Glu | Gln | Gln | Leu | Tyr | Ser |
| | | | 405 | | | | | 410 | | | | | 415 | | |
| Ala | Gln | Ala | Ile | Leu | Ala | Ser | Ala | Lys | Tyr | Thr | Tyr | Ile | Lys | Ser | Trp |
| | | | 420 | | | | 425 | | | | | 430 | | | |
| Ile | Thr | Leu | Leu | Ser | Asp | Ser | Gly | Thr | Leu | Asp | Glu | Lys | Asp | Val | Leu |
| | | 435 | | | | | 440 | | | | 445 | | | | |
| Arg | Val | Ala | Gln | Tyr | Phe | Tyr | Pro | Gln | Ser | Ile | Thr | Thr | Tyr | Ser | Leu |
| 450 | | | | | 455 | | | | | 460 | | | | | |

GENE PARTICIPATING IN THE MECHANISM OF SECRETION OF ESTERASE

CROSS-REFERENCE TO RELATED APPLICATION

This is a Continuation-in-Part application of U.S. Ser. No. 08/620,605 filed on Mar. 22, 1996.

FIELD OF INVENTION

This invention relates to a gene DNA coding for a polypeptide which participates in the mechanism of secretion of esterase by a microorganism of the genus Serratia, a recombinant plasmid containing said gene, a novel microorganism transformed with the recombinant plasmid, a novel microorganism containing simultaneously the above recombinant plasmid and a recombinant plasmid containing a gene coding for an esterase, and a process for producing an esterase by cultivating the novel microorganisms.

PRIOR ART

Recently, it has frequently been tried to utilize enzymes such as esterase in hydrolysis reaction. For such a purpose, there are known various esterases, for example, esterases originated from animals (e.g. pig liver, pig pancreas, etc.), and esterases produced by microorganisms, such as *Arthrobacter globiformis, Geotrichum candidum, Candida cylindracea, Pseudomonas fluorescens*, etc. Further, it is known that an esterase produced by *Serratia marcescens* is prepared by a recombinant DNA technology.

However, the known esterases or known methods for producing esterase have various problems. For instance, animal-origin esterases are very expensive, and the microorganisms-origin esterases had problems such that they were disadvantageous in activity, stability, or specificity, or that the esterase-producing microorganism had no high productivity. Moreover, even by using a gene recombinant microorganism, it is not necessarily easy to increase the esterase productivity thereof to the level applicable for industrial production merely by magnifying the esterase gene. Besides, even though the productivity of esterase is increased, the extracellular secretion of esterase is occasionally insufficient, and thereby complicated procedure is required for recovery of the enzyme.

As a result of various investigations, the present inventors have succeeded in obtaining a gene (DNA) coding for a polypeptide which participates in the mechanism of secretion of esterase by a microorganism of the genus Serratia and further have found that the esterase-producing microorganisms can show remarkably increased capability of secretion of esterase by transforming said microorganism with a recombinant plasmid containing said DNA. The present invention has been accomplished based on these new findings.

BRIEF SUMMARY OF THE INVENTION

An object of the present invention is to provide a gene coding for a polypeptide which participates in the mechanism of secretion of esterase produced by a microorganism of the genus Serratia. Another object of the invention is to provide a recombinant plasmid prepared by inserting said gene into a vector plasmid and further a transformant containing said recombinant plasmid. A further object of the invention is to provide a method for the production of an esterase by cultivating said transformant and collecting the esterase accumulated outside and inside the cells of the transformant.

DETAILED DESCRIPTION OF THE INVENTION

Figure 1:
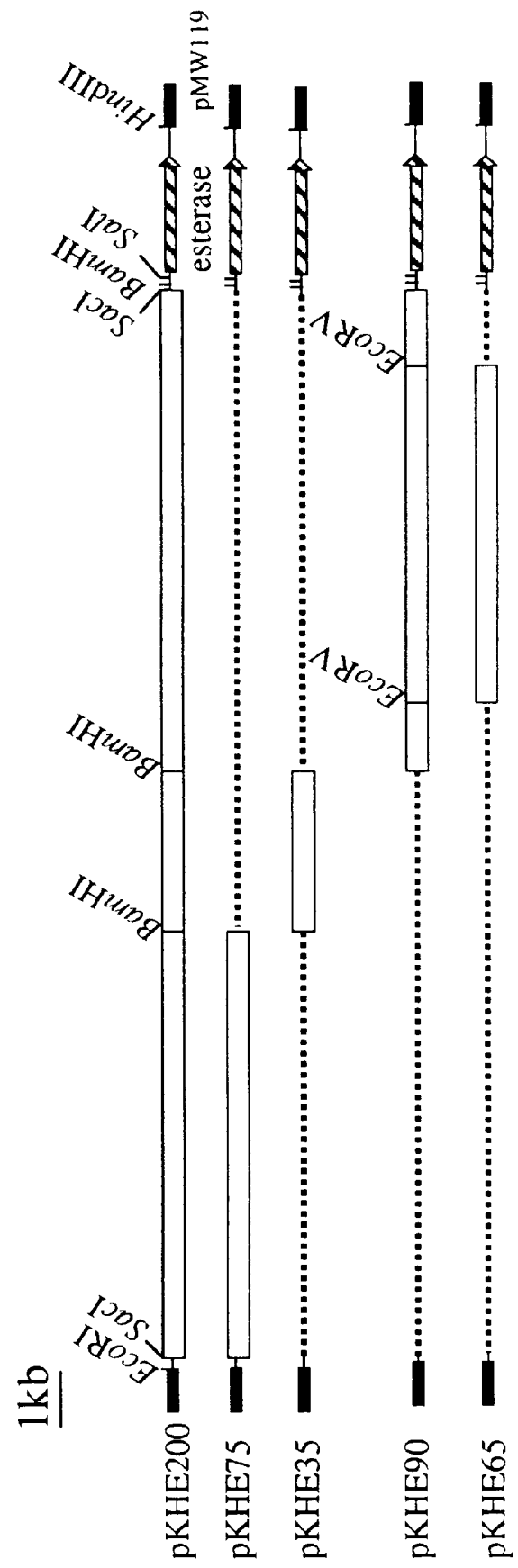
FIG. 1 shows restriction endonuclease maps of each of plasmid DNAs pPKHE200, pPKHE75, pPKHE35, pPKHE90 and pPKHE65 which were isolated from the recombinant cells in Example 2.

The gene encoding a polypeptide which participates in the mechanism of secretion of esterase, that is, is required for secretion of esterase, (hereinafter, referred to as "esterase secretory gene") is a double stranded DNA including three open reading frames (ORF) within the sequence, specifically DNA having the nucleotide sequence shown in SEQ ID NO:1 hereinafter.

The donor microorganisms for such an esterase secretory gene include any microorganisms belonging to the genus Serratia which has an esterase productivity, for example, *Serratia marcescens* Sr41 (FERM BP-487), *Serratia liquefaciens* ATCC 27592, *Serratia marcescens* ATCC 13880, *Serratia marcescens* ATCC 14764, *Serratia marcescens* ATCC 19180, *Serratia marcescens* ATCC 21074, *Serratia marcescens* ATCC 27117, *Serratia marcescens* ATCC 21212, etc.

The vector plasmid into which the esterase secretory gene is inserted includes any plasmids being replicable in transformed cells. Among them, preferred example of said plasmid includes plasmids which have a copy number of 1 to several thousands and contain a resistant marker against antibiotics such as ampicillin, kanamycin, chloramphenicol, and further contain an appropriate promoter such as lac, tac, or trp. Moreover, the vector plasmids may further contain a plasmid-stabilizing gene such as par and parB.

These vector plasmids include, for example, pLG339 [Gene, Vol. 18, 332 (1982)], pBR322 [Gene, Vol. 2, 95 (1977)], pUC18 [Gene, Vol. 33, 103 (1985)], pUC19 [Gene, Vol. 33, 103 (1985)], pHSG298 [Gene, Vol. 61, 63 (1987)], pHSG299 [Gene, Vol. 61, 63 (1987)], and the like.

The above vector plasmids are commercially available or can be obtained from microbial cells containing these plasmids by a conventional method, for example, by "cleared lysate method" (cf. Yasuyuki Takagi, "Procedure for Experiment in Genetic Engineering", page 125, published by Kodansha, 1980), or by "alkaline lysis method" [cf. Maniatis et al., "Molecular Cloning", page 368, Cold Spring Harbor Laboratory, U.S.A. (1982)].

The host microorganisms (both for the recombination of plasmids and for the expression of the desired esterase), include any microorganisms which can be transformed with the recombinant plasmid and can replicate the plasmid therein, and can express the gene on the plasmid and can produce a functional protein. These host microorganisms include, for example, microorganisms belonging to the genus Serratia or the genus Escherichia, specifically *Serratia marcescens* Sr41 and various mutant strains derived therefrom, for example, *Serratia marcescens* M-1 (FERM BP-4068), *Serratia marcescens* TT392 [cf. Journal of Bacteriology, Vol. 161, 1 (1985)], or *Escherichia coli* K12 DH5 [cf. Maniatis et al., "Molecular Cloning", 2nd volume, A10, Cold Spring Harbor Laboratory, U.S.A. (1989)].

In addition, there may be used as the host microorganisms any other microorganisms containing a recombinant plasmid to which an esterase gene of the genus Serratia is inserted, for example, *Serratia marcescens* TA5025 (FERM BP-4067).

The chromosomal DNA containing the esterase secretory gene can easily be obtained from microorganisms containing said gene by a conventional method, for example, by treating the microbial cells with a lysozyme and further with a surfactant (e.g. sodium lauryl sulfate, sodium N-lauroyl sarcosinate, etc.), extracting the cells thus treated with an organic solvent (e.g. phenol, chloroform, diethyl ether, etc.) to remove proteins, and then precipitating the DNA with ethanol [cf. Journal of Molecular Biology, Vol. 3, 208 (1961), and Biochimica et Biophysica Acta, Vol. 72, 619 (1963)].

The recombinant plasmid comprising the chromosomal DNA containing an esterase secretory gene and the vector plasmid DNA can easily be prepared by a conventional method, for example, by cleaving the chromosomal DNA and the plasmid DNA with an appropriate restriction endonuclease (e.g. EcoRI, BamHI, HindIII, SalI, SacI, etc.) and then treating the resultant with DNA ligase (e.g. T4 DNA ligase, *E. coli* DNA ligase, etc.), if required, after treating the resultant with a terminal transferase or DNA polymerase, subjecting to said treatment with DNA ligase [cf. Methods in Enzymology, Vol. 68, 41 (1979), and Yasuyuki Takagi, "Procedure for Experiment in Genetic Engineering", page 135, published by Kodansha, 1980].

Selection of the desired recombinant plasmid containing the esterase secretory gene from a mixture of recombinant plasmids obtained by the above procedure can be done as follows.

Microbial cells being restriction endonuclease deficient and having esterase productivity, for example *Escherichia coli* K12 DH5 harboring a recombinant plasmid which contains an esterase gene (e.g. pLIPE111 disclosed in Japanese Patent First Publication (Kokai) No. 344891/1993, etc.) are transformed with the esterase-secretory gene-containing recombinant plasmids, and the thus-transformed cells are spread onto an agar medium containing an emulsified triglyceride in which the cell can grow, for example, a nutrient agar medium containing tributyrin emulsified with polyoxyethylene cetyl alcohol ether (Brij 58) and also containing a prescribed concentration of an antibiotic. After incubation at 30 to 37° C. for 1 to 2 days, the colony of a transformant around which a large clear zone is formed is isolated.

The above introduction of the recombinant plasmid into the host microorganism is carried out by a conventional method, for example, by treating the host cells with an aqueous calcium chloride solution at a low temperature to increase the membrane permeability of the cells and then introducing the recombinant plasmid into the host cells [cf. Journal of Molecular Biology, Vol. 53, 159 (1970)], or by an electroporation method.

The desired transformant may also be selected by the procedure comprising transforming cells of a microorganism (e.g. *Escherichia coli* K12 DH5, etc.) with a recombinant plasmid produced by inserting both of a DNA participating in the esterase secretory mechanism and of an esterase gene into a single vector plasmid, and then treating the resultant transformed cells in the same manner as described above.

Then, the plasmid DNA is extracted from the transformant by "alkaline lysis method" to give the recombinant plasmid, i.e. a plasmid produced by inserting an esterase gene of *Serratia marcescens* into a vector plasmid.

In order to make the transformation efficient, the recombinant plasmid thus obtained is modified in a microorganism which is restriction endonuclease deficient and is the same species of the host microorganism to be used for expressing the esterase. That is, when the host microorganism to be used is *Serratia marcescens* Sr41, the recombinant plasmid obtained above is introduced into *Serratia marcescens* TT392, which is a restriction enzyme deficient strain. The recombinant plasmid thus modified is isolated from the microorganism. The modified recombinant plasmid is then introduced into a host microorganism to obtain the desired transformant suitable for the production of the desired esterase.

The introduction of the recombinant plasmid into the host microorganism can easily be done by the method of Takagi & Kizumi [cf. Journal of Bacteriology, Vol. 161, 1 (1985)], and the isolation of the plasmid can be done, for example, by alkaline lysis method. Besides, the desired transformant may be obtained by isolating the colony expressing antibiotics resistance. The host microorganisms to be used for said transformation include the above-mentioned microorganisms but are preferably strains having high esterase productivity.

The transformed microorganisms obtained by the above-mentioned method are, for example, *Serratia marcescens* TA5030 which is obtained by introducing a recombinant plasmid into *Serratia marcescens* Sr41 wherein said recombinant plasmid being obtained by inserting an about 2.6 kb SalI-BstPI DNA fragment containing an esterase gene and an about 6.5 kb EcoRV—EcoRV DNA fragment containing an esterase secretory gene into a vector plasmid pMW119; *Serratia marcescens* TBS90 which is obtained by introducing a recombinant plasmid into *Serratia marcescens* Sr41 wherein said recombinant plasmid being obtained by inserting an about 2.6 kb SalI-BstPI DNA fragment containing an esterase gene and an about 9.0 kb BamHI-SacI DNA fragment containing an esterase secretion gene into a vector plasmid pMW119. These transformed strains all have the same morphological characteristics as those of the host microorganism *Serratia marcescens* Sr41.

The production of esterase with the transformed microorganism obtained above is carried out by cultivating the microorganism in a medium and collecting the esterase outside and inside the cells of the microorganism.

The medium used for the production of esterase includes any conventional medium wherein the microorganism can grow. Suitable medium contains a carbon source such as saccharides (e.g. glucose, sucrose, molasses, etc.), organic acids (e.g. fumaric acid, citric acid, etc.), alcohols (e.g. glycerol, etc.), or amino acids (e.g. alanine, glutamine, asparagine, etc.) and a nitrogen source such as inorganic ammonium salts (e.g. ammonium sulfate, ammonium chloride, etc.), urea, peptone, corn steep liquor, yeast extract, casein hydrolysate, and the like. The carbon source is usually contained in an amount of 1 to 15 (W/V)% based on the medium, and the nitrogen source is usually contained in an amount of 0.1 to 2.0 (W/V)% based on the medium. The medium may optionally contain further an appropriate amount of an inorganic salt (e.g. phosphate, magnesium salt, potassium salt, calcium salt, etc.) and/or a metallic ion (e.g. iron, manganese, copper, zinc, etc.). In case of a synthetic medium, it may further contain vitamins or amino acids, and further, inducers for esterase production (e.g. vegetable oils, surfactants, etc.), defoaming agents, antibiotics which are suitable for stabilizing the recombinant plasmid in microorganisms. The medium is preferably adjusted to a pH 5 to 8.

The cultivation of the transformed microorganism is carried out by a conventional method. For example, the microorganism is inoculated into a medium and is cultivated by shaking culture, aeration culture, standing culture, continuous culture, or the like. The cultivation conditions may vary depending on the kinds of the medium and cultivation methods, but may be any conditions suitable for growth of the microorganism, usually at the initial pH 5–8, at 20 to 40° C., for 1 to 2 days.

The esterase produced outside and inside the cultivated cells is collected by a conventional method. For example, the esterase contained in the medium is collected by means of salting out with an inorganic salt, precipitation with an organic solvent, absorption or desorption with ion exchange resin and various column chromatography, gel filtration, use of protein-precipitating agent, or a combination of these methods. The esterase accumulated within the cells is obtained by firstly disrupting the cells by a physical method such as frictional disrupting device (Dyno Mill) or a chemical means such as treatment with lysozyme, and then collecting the esterase in the cell extract by the above-mentioned method.

The esterase secretory gene of this invention is not limited to those of the DNA sequences disclosed specifically in the present specification but includes any gene having a DNA sequence obtained by modifications in the sequence such as insertion, deletion or substitution. That is, the esterase secretory gene may artificially be modified directly in a test tube by using a synthetic mutated DNA primer designed on the basis of the DNA sequence of the gene encoding an esterase specifically disclosed herein, or by using a chemical mutating agent such as formic acid, hydrazine sulfite. Further, a mutant gene may be obtained by treating an esterase producing strain with NTG or UV.

EXAMPLES

The present invention is illustrated by the following Examples but should not be construed to be limited thereto.

In the Examples, the esterase activity was measured by a convenient method (using Lipase Kit S wherein the substrate being dimercaprol tributyrate, manufactured by Dainippon Pharmaceutical Co., Ltd., Japan). It may also be measured by another method comprising subjecting the product to enzymatic reaction in olive oil (as a substrate) at pH 8.0, 37° C. for 20 minutes, and then measuring the amount of formed fatty acid, wherein the unit of esterase activity is expressed as $\mu$mols of fatty acid formed per minute.

Besides, the medium used in Examples has the following formulation, wherein "%" is W/V % unless specified otherwise.

LB medium: 1.0% of Bactotryptone (manufactured by Difco), 0.5% of Bacto Yeast Extract (manufactured by Difco), and 0.5% of sodium chloride.

LBG plate medium: 1.0% of Bactotryptone (manufactured by Difco), 0.5% of Bacto Yeast Extract (manufactured by Difco), 0.5% sodium chloride, and 1.0% of Gellan Gum (manufactured by Wako Pure Chemical Industries, Ltd., Japan).

Tributyrin-containing LBG plate medium: LBG plate medium containing 0.5 v/v % of tributyrin, 0.5% of polyoxyethylene cetyl alcohol ether, and 0.005% of ampicillin.

Esterase producing medium: 1.0% of dextrin, 2.0% of meast, 0.2% of ammonium sulfate, 0.1% of potassium dihydrogen phosphate, 0.05% of magnesium sulfate heptahydrate, 0.01% of calcium chloride dihydrate, 0.001% of ferrous sulfate heptahydrate, 0.5% of Tween 80, and 0.1% of colorin.

EXAMPLE 1

(1) Preparation of Chromosomal DNA Containing an Esterase Secretory Gene:

*Serratia marcescens* Sr41 (FERM BP-487) was subjected to aerobic shaking culture in LB medium (200 ml) at 30° C. overnight, and then the cells were collected by centrifugation. The cells were suspended in 0.9% aqueous sodium chloride solution (200 ml) once and then collected by centrifugation in order to wash them. The cells thus washed were suspended in an aqueous solution of 50 mM Tris-HCl-50 mM disodium ethylenediamine tetraacetate (pH 7.5, 200 ml) containing 200 mg of lysozyme, and the mixture was allowed to stand at room temperature for one hour.

To the mixture was added sodium lauryl sulfate in a concentration of 0.5%, and thereto was further added Protenase K, and the mixture was mildly shaken at 50° C. for 3 hours to lyse the cells. The mixture was extracted twice with an equal volume of phenol saturated with an aqueous solution of 10 mM Tris-HCl-1 mM disodium ethylenediamine tetraacetate (pH 8.0) (hereinafter, referred to as "TE"), and further extracted twice with a mixture of equal volume of TE-saturated phenol and chloroform, and then the resultant aqueous phase was subjected to precipitation with ethanol. The precipitate was dissolved in TE to prepare a TE solution containing 2.5 mg of the chromosomal DNA containing an esterase secretory gene.

(2) Preparation of a Recombinant Plasmid DNA:

The chromosomal DNA prepared in the above (1) (20 $\mu$g) was completely digested with restriction endonuclease SacI, which was extracted twice with a mixture of equal volume of TE-saturated phenol and chloroform. To the mixture was added 0.5 volume of 7.5 M ammonium acetate, and the DNA was recovered by precipitating with two times volume of ethanol.

A plasmid vector pMWE121 was prepared by inserting an about 2.6 kb genome DNA fragment (SalI-BstPI fragment) containing an esterase gene originated from *Serratia marcescens* Sr41 into a vector plasmid pMW119. DNA (0.5 $\mu$g) of said plasmid vector pMWE121, which was completely digested with the same restriction enzyme as above, was dephosphated by treating with alkaline phosphatase (manufactured by Takara Shuzo Co., Ltd., Japan, 0.4 unit) at 56° C. for one hour, and the resultant was extracted twice with a mixture of equal volume of TE-saturated phenol and chloroform, and thereto was added 0.5 volume of 7.5M ammonium acetate, and then the vector plasmid DNA was recovered by precipitating with two times volumes of ethanol. The dephosphated plasmid vector thus obtained was mixed with the chromosomal DNA obtained above (3 $\mu$g) and ligated with a DNA ligation kit (manufactured by Takara Shuzo Co., Ltd.) at 4° C. for 16 hours to give the recombinant plasmid DNA.

(3) Transformation with the Recombinant Plasmid and Preparation of Colony Bank with *E. coli* Host:

The cells of *E. coli* DH5 were treated by the method of Hanahan [cf. Journal of Molecular Biology, Vol. 166, 557 (1983)] and thereto was added the reaction mixture containing a plasmid DNA obtained in the above (2), by which the transformation was effected. The cells thus treated were spread onto LBG plate medium containing ampicillin (50 $\mu$g/ml), and they were incubated at 37° C. overnight to give the transformant (about 50,000 strains) containing recombinant plasmids inserted with fragments of the chromosomal DNA of *Serratia marcescens* Sr41.

(4) Isolation and Identification of a Transformant Strain Containing an Esterase Secretory Gene:

When an esterase producing strain is inoculated to a tributyrin-containing LBG plate medium, the esterase produced in the medium decomposes tributyrin to give fatty acids, by which the triglyceride emulsion around the colony is modified to form a circular clear zone around the colonies. By utilizing this phenomenon, the screening of transformants was effected.

The transformants (about 50,000 strains) obtained in the above (3) were inoculated to a tributyrin-containing LBG plate medium, which was incubated at 37° C. overnight, by which one strain forming a clear zone was isolated from the DNA bank of SacI.

The formation of this clear zone will be owing to the increase of ability of extracellulor secretion of esterase by introducing the recombinant plasmid containing an esterase secretory gene, because when *Serratia marcescens* Sr41 was inoculated to a tributyrin-containing LBG plate medium and incubated at 37° C. overnight, the formation of a clear zone was observed, but when the untransformed *E. coli* DH5 and the *E. coli* DH5 carrying a plasmid vector pMWE121 were inoculated to a tributyrin-containing LBG plate medium and incubated at 37° C. overnight, no formation of a clear zone was observed.

Besides, the transformant being capable of formation of a clear zone was cultivated in a LB medium (60 ml) containing ampicillin (200 μg/ml) by aerobic shaking culture at 37° C. overnight, and the esterase activity of the supernatant of the culture mixture was measured by the convenient method. As a result, there was observed 34,800 units of esterase activity.

Moreover, the supernatant of the above culture mixture was subjected to an electrophoresis with SDS polyacrylamide gel, and the resultant was subjected to Western blotting analysis by using rabbit antiesterase antibody to an esterase produced by *Serratia marcescens*. As a result, the product showed a new band, which was not shown in the product from *E. coli* DH5 containing only vector plasmid, at the same position as that in the purified standard esterase obtained from the supernatant of the culture of *Serratia marcescens* Sr41.

EXAMPLE 2

Analysis of Plasmid:

A plasmid DNA was prepared from the cells of the transformant obtained in Example 1-(4) by a conventional method [cf. Maniatis et al., "Molecular Cloning", page 368, Cold Spring Harbor Laboratory, U.S.A. (1982)], cleaved with various restriction endonucleases and then subjected to an agarose gel electrophoresis. As a result, it was confirmed that this plasmid (hereinafter, referred to as "pKHE200") contained a SacI DNA fragment of about 20.0 kb in addition to about 2.6 kb SalI-BstPI DNA fragment containing an esterase gene originated from *Serratia marcescens*.

The restriction endonuclease map of the SacI DNA fragment of about 20.0 kb contained in said pKHE200 is shown in the accompanying FIG. 1.

The SacI DNA fragment of about 20.0 kb of the plasmid pKHE200 was cleaved with various restriction endonucleases, and each DNA fragment was subcloned into plasmid vector pMWE121, followed by transformation of *E. coli* DH5 with the recombinant plasmid thus obtained. The transformants were cultivated in a tributyrin-containing LBG plate medium in the same manner as described above, and it was determined whether a clear zone was formed or not.

The restriction endonuclease maps of each DNA fragment are shown in the accompanying FIG. 1. As to *E. coli* DH5 transformed with the plasmid containing BamHI-SacI DNA fragment of about 9.0 kb (pKHE90) and the plasmid containing EcoRV—EcoRV DNA fragment of about 6.5 kb (pKHE65), there were observed the formation of a clear zone and esterase activity (measured by the convenient method). However, as to *E. coli* DH5 transformed with the plasmid containing SacI-BamHI DNA fragment of about 7.5 kb (pKHE75) and with the plasmid containing BamHI—BamHI DNA fragment of about 3.5 kb (pKHE35), there was observed neither the formation of a clear zone nor esterase activity (measured by the convenient method).

It was found from the above results that the esterase secretory gene originated from *Serratia marcescens* Sr41 was present in the EcoRV—EcoRV DNA fragment of about 6.5 kb.

The *E. coli* DH5 transformed with the plasmid pKHE65 has been deposited to National Institute of Bioscience and Human-Technology, Agency of Industrial Science and Technology on Feb. 9, 1996 as accession number FERM BP-5385 (designated "*Escherichia coli* TA5029").

EXAMPLE 3

Analysis of Clone DNA:

[Determination of nucleotide sequence]

The recombinant plasmid pKHE65 was treated with Kilobase Deletion Kit (manufactured by Takara Shuzo Co., Ltd.) to prepare various deletion plasmids. These plasmids thus obtained were subjected to annealing of a primer, synthesis of complementary chain with Klenow fragment of DNA polymerase [labelled with ($\alpha$-$^{32}$P)dCTP (14.8×10$^6$ Bq/pmol, 74×10$^4$ Bq)] according to the dideoxy chain termination method of Sanger et al. [Proc. Natl. Acad. Sci. USA, Vol. 74, 5463 (1977)], and the nucleotide sequences thereof were determined based on the data of an electrophoresis with an 8% urea-modified polyacrylamide gel and autoradiography.

As a result, it has been found that the DNA sequence of the esterase secretory gene originated from *Serratia marcescens* Sr41 comprises 4547 base pairs from the initiation codon GTG to the codon CTA as shown in SEQ ID NO:1, which includes DNA regions (ORF) coding for three kinds of polypeptides which participate in the mechanism of secretion of esterase. (It is assumed that these three ORFs compose a pair of operon.)

Besides, the amino acid sequences of the polypeptides coded by each ORF are shown in SEQ ID NO: 2, 3 and 4, respectively.

EXAMPLE 4

Preparation of a Strain Having High Esterase Productivity:

The plasmid pKHE65 was introduced into a restriction endonuclease-deficient strain, *Serratia marcescens* TT392, to give a transformed strain. The pKHE65 plasmid DNA modified with *Serratia marcescens* was extracted from the cells of the transformed strain by "alkaline lysis method". Then, *Serratia marcescens* Sr41 cells were transformed with the plasmid DNA obtained above by electroporation method to give a transformant *Serratia marcescens* TA5030). The thus-obtained transformant (one platinum loop) was inoculated to an esterase-producing medium containing ampicillin (500 μg/ml) and subjected to reciprocating shaking culture (shaking amplitude 7 cm, 120 r.p.m.) at 30° C. for 20 hours. The culture broth was centrifuged to give a supernatant having an esterase activity of about 3.5×10$^5$ unit/ml (measured by the convenient method). This strain had about 10 times higher esterase productivity than the host strain *Serratia marcescens* Sr41 and further about 2 times higher esterase productivity than *Serratia marcescens* Sr41 containing recombinant plasmid pMWE121 (used as a vector plasmid).

EFFECTS OF THE INVENTION

The microorganism transformed with a recombinant plasmid containing an esterase secretory gene of the present invention have remarkably excellent capability of extracellular secretion of esterase. Accordingly, when an esterase-producing microorganism harboring a recombinant plasmid which contains an esterase gene is further transformed with the recombinant plasmid which contains the esterase secretory gene of the present invention, there can be obtained a microorganism having excellent properties in both of esterase productivity and extracellulor secretion of esterase, and the cultivation of said transformant can give the desired esterase on an industrial scale.

What is claimed is:

1. An isolated gene encoding a polypeptide, having an amino acid sequence as shown in SEQ ID NOS: 2, 3 or 4, which is required for secretion of esterase originated from a microorganism of the genus Serratia.

2. The gene as claimed in claim 1 which comprises a DNA having a sequence as shown in SEQ ID NO: 1.

3. A recombinant plasmid prepared by inserting the gene as set forth in claim 1 or claim 2 into a vector plasmid.

4. A microorganism transformed with the recombinant plasmid as set forth in claim 3.

5. A microorganism which is obtained by transforming a host microorganism with a recombinant plasmid, said recombinant plasmid being prepared by inserting into a vector plasmid (i) a gene encoding an esterase originated from a microorganism of the genus Serratia and (ii) the gene as set forth in claim 1 or 2.

6. A microorganism which is obtained by transforming a host microorganism with (i) a recombinant plasmid prepared by inserting a gene encoding an esterase originated from a microorganism of the genus Serratia into a vector plasmid and (ii) a recombinant plasmid prepared by inserting the gene as set forth in claim 1 or 2 into a vector plasmid.

7. The microorganism as claimed in claim 5, wherein the host microorganism is a microorganism of the genus Serratia or a microorganism of the genus Echerichia.

8. A method for production of an esterase, which comprises cultivating the microorganism as set forth in claim 5 in a medium, and collecting the esterase accumulated inside the cells and in the surrounding medium.

9. The microorganism as claimed in claim 6, wherein the host microorganism is a microorganism of the genus Serratia or a microorganism of the genus Echerichia.

10. A method for production of an esterase, which comprises cultivating the microorganism as set forth in claim 6 in a medium, and collecting the esterase accumulated inside the cells and in the surrounding medium.

11. A method for production of an esterase, which comprises cultivating the microorganism as set forth in claim 7 in a medium, and collecting the esterase accumulated inside the cells and in the surrounding medium.

12. A method for production of an esterase, which comprises cultivating the microorganism as set forth in claim 9 in a medium, and collecting the esterase accumulated inside the cells and in the surrounding medium.

* * * * *

UNITED STATES PATENT AND TRADEMARK OFFICE
CERTIFICATE OF CORRECTION

PATENT NO. : 5,922,568
DATED : July 13, 1999
INVENTOR(S) : Shibatani et al.

It is certified that error appears in the above-identified patent and that said Letters Patent is hereby corrected as shown below:

Please insert categories "[73] Assignee" and "[30] Foreign Application Priority Data" as follows:

-- [73] Assignee: Tanabe Seiyaku Co., Ltd., Osaka, Japan --.

-- [30] Foreign Application Priority Data

March 23, 1995 [JP] Japan .......................... 63772/1995 --.

In claim 7, line 3, change "Echerichia" to -- Escherichia --.

In claim 9, line 3, change "Echerichia" to -- Escherichia --.

Signed and Sealed this

Seventeenth Day of April, 2001

Attest:

NICHOLAS P. GODICI

Attesting Officer

Acting Director of the United States Patent and Trademark Office